United States Patent [19]

Nakano et al.

[11] Patent Number: 4,923,990

[45] Date of Patent: May 8, 1990

[54] PYRINDAMYCINS A AND B AND DUOCARMYCIN A ANTIBIOTICS DERIVED FROM CERTAIN STREPTOMYCES CULTURE

[75] Inventors: Hirofumi Nakano; Isami Takahashi, both of Tokyo, Japan; Michio Ichimura, Nashville, Tenn.; Isao Kawamoto, Kanagawa, Japan; Kozo Asasno, Ibaraki, Japan; Fusao Tomita, Tokyo, Japan; Hiroshi Sano, Tokyo, Japan; Toru Yasuzawa, Tokyo, Japan; Makoto Morimoto, Shizouka, Japan; Kazuhisa Fujimoto, Kanagawa, Japan

[73] Assignee: Kyowa Hakko Kogyo Co., Ltd., Tokyo, Japan

[21] Appl. No.: 242,788

[22] Filed: Sep. 9, 1988

Related U.S. Application Data

[63] Continuation-in-part of Ser. No. 143,138, filed as PCT JP87/00247 on Apr. 17, 1987, published as WO87/06265 on Oct. 22, 1987, abandoned.

[30] Foreign Application Priority Data

Apr. 17, 1986 [JP] Japan ............................ 61-89031
Apr. 24, 1986 [JP] Japan ............................ 61-95649

[51] Int. Cl.$^5$ ............... C07D 487/04; C07D 519/00; C07 519/00; C12P 17/18
[52] U.S. Cl. ................................. 546/84; 548/421; 435/119

[58] Field of Search ..................... 546/84; 548/421

[56] References Cited

U.S. PATENT DOCUMENTS

| 4,169,888 | 10/1969 | Hanka et al. ............. 424/121 |
| 4,400,518 | 8/1983 | Wieringa ............... 548/433 |
| 4,413,132 | 11/1983 | Wieringa ............... 548/491 |
| 4,423,228 | 12/1983 | Wieringa ............... 548/421 |
| 4,423,229 | 12/1983 | Wieringa ............... 548/421 |
| 4,423,230 | 12/1983 | Wieringa ............... 548/433 |

FOREIGN PATENT DOCUMENTS

| 60-193989 | 2/1985 | Japan ................... 548/433 |
| 2086394 | 5/1982 | United Kingdom ....... 424/121 |
| 88/04659 | 6/1988 | World Int. Prop. O. ... 548/433 |

OTHER PUBLICATIONS

Adv. Enzyme Regul. 25, 141–155 (1986), Wieringa, et al., "Antitumor Activity . . . ".

J. Med. Chem. 31, 590–603 (1988), Warpehoski et al., "Stereo Electronic Factors . . . ".

*Primary Examiner*—Alan L. Rotman
*Attorney, Agent, or Firm*—Michael N. Meller

[57] ABSTRACT

The present invention relates to DC-88A and DC-89A1 and their production. These compounds are obtained by fermentation of microorganisms belonging to the genus Streptomyces. These compounds have antibacterial and anti-tumor activities and are useful as medicaments.

2 Claims, 4 Drawing Sheets

PYRINDAMYCINS A AND B AND DUOCARMYCIN A ANTIBIOTICS DERIVED FROM CERTAIN STREPTOMYCES CULTURE

This is a continuation-in-part of U.S. patent application Ser. No. 143,138, filed as PCT JP87/00247 on Apr. 17, 1987, published as WO87/06265 on Oct. 22, 1987, now abandoned.

TECHNICAL FIELD

The present invention relates to novel compounds DC-88A and DC-89A1 and a process for preparing the same by culturing microorganisms belonging to the genus Streptomyces. These compounds have strong antibacterial and anti-tumor activities. Compounds DC-88A and DC-89A1 are duocarmycin A and duocarmycin C1, respectively.

BACKGROUND ART

As the low-molecular compounds having antibacterial and anti-tumor activities and obtained from microorganisms or plants, many compounds such as anthracycline compounds, anthraquinone compounds and mitomycin compounds have so far been reported [CRC Handbook of Antibiotic Compounds, 1981, CRC Press, U.S.A.].

In order to obtain superior antibiotics and antitumor compounds, which are always in demand, many microorganisms have been isolated from nature and examined for the productivity of antibiotics. As a result, it has been found that novel antibiotics having an anti-tumor activity are produced by culturing a microorganism isolated from the soil in Sunto-gun, Shizuoka Prefecture (hereinafter referred to as DO-88 strain) and a microorganism isolated from the soil in Mt. Rokko, Hyogo Prefecture (hereinafter referred to as DO-89 strain) in a medium. These compounds have been named DC-88A and DC-89A1, respectively.

DISCLOSURE OF THE INVENTION

In accordance with the present invention, novel substances DC-88A and/or DC-89A1 having antibacterial and anti-tumor activities are obtained by culturing microorganisms of the genus Streptomyces which are capable of producing DC-88A and/or DC-89A1 in a medium. Physicochemical properties of the substances are shown below.

DC-88A (a) Molecular formula: $C_{26}H_{25}N_3O_8$
(b) Mass spectrum: SIMS m/z 510 (M+3)+, 234 (base peak) (measured with glycerol as matrix); m/z 508 (M+1)+, 234 (base peak) (measured with sulfolane as matrix). High resolution EI-MS: Found: 507.1624; Calculated for $C_{26}H_{25}N_3O_8$: 507.1639.
(c) Ultraviolet absorption spectrum: Shown in FIG. 1 (measured in MeOH)
(d) Infrared absorption spectrum: Shown in FIG. 2 (measured in CHCl$_3$)
(e) Solubility: Soluble in methanol, ethanol, acetone, chloroform, ethyl acetate and DMSO; and sparingly soluble in water and hexane
(f) $^1$H-NMR spectrum (400 MHz, measured in CDCl$_3$, internal standard TMS): δ(ppm) 9.38 (1H, br, s), 7.17 (1H, s), 6.94 (1H, d, J=2.4 Hz), 6.78 (1H, s), 6.21 (1H, br, s), 4.43 (2H, AB in ABX, $J_{AB}$=10.0 Hz), 4.07 (3H, s), 3.94 (3H, s), 3.89 (3H, s), 3.75 (3H, s), 3.06 (1H, m), 2.24 (1H, dd, J=7.6, 3.9 Hz), 1.67 (3H, br, s), ca. 1.3 (1H)
(g) $^{13}$C-NMR spectrum (100 MHz, measured in CDCl$_3$, internal standard TMS): δ(ppm) 194.8, 179.8, 167.9, 165.2, 164.4, 161.2, 150.6, 141.3, 138.9, 128.2, 126.6, 123.3, 113.2, 112.0, 108.2, 97.7, 71.3, 61.5, 61.2, 56.3, 55.3, 53.4, 30.7, 22.3, 22.1, 21.1
(h) R$_f$ value: 0.46 (toluene:acetone=7:3 V/V, silica gel)

DC-89A1

(a) Elementary analysis: C: 56.5, H: 4.7, N: 7.1
(b) Molecular formula: $C_{26}H_{26}N_3O_8Cl_1$
(c) Molecular weight: 543 (measured by mass spectrum method)
(d) Melting point: 157.5°–158.5° C.
(e) Ultraviolet absorption spectrum: Shown in FIG. 3 (measured in CH$_3$OH)
(f) Infrared absorption spectrum: Shown in FIG. 4 (measured in CHCl$_3$)
(g) PMR spectrum (in DMSO-d6, internal standard TMS): δ(ppm) 11.54 (1H, broad), 9.88 (1H, s), 7.39 (1H, s), 6.91 (1H, broad s), 6.87 (1H, s), 6.58 (1H, broad d), 4.76 (1H, m), 4.35 (1H, broad dd), 3.96 (1H, broad d), 3.92 (3H, s), 3.777 (3H, s), 3.775 (3H, s), 3.61 (3H, s), 3.53 (1H, broad dd), 3.25 (1H, broad dd), 1.47 (3H, broad s)
(h) CMR spectrum (in CDCl$_3$, internal standard TMS): δ(ppm) 196.6, 171.2, 164.5, 151.6, 150.2, 141.6, 140.8, 138.8, 129.3, 128.8, 125.9, 123.0, 118.1, 117.0, 116.9, 108.2, 97.7, 71.1, 61.5, 61.2, 56.2, 53.6, 53.4, 52.5, 33.2, 21.9
(i) Solubility: readily soluble in methanol, ethanol, ethyl acetate, acetone, chloroform and DMSO; and sparingly soluble in water and n-hexane We have determined the structure of DC-88A and DC-89A1 and they are represented by the following formulae:

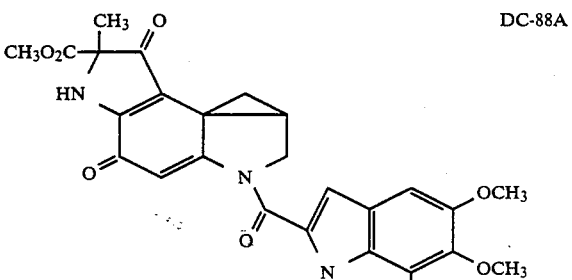

DC-88A and

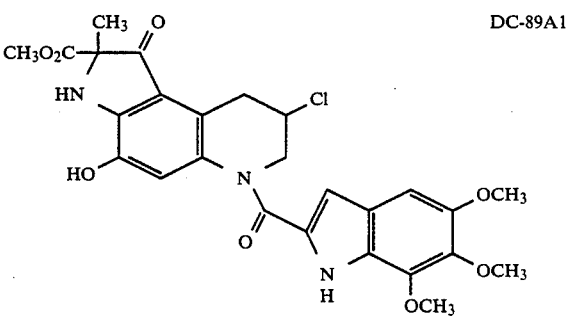

DC-89A1

The $R_f$ values of DC-89A1 with thin layer chromatography [silica gel (Kieselgel 60 Art. 5715, E. Merck, West Germany), developed for one hour at room temperature] are shown in Table 1.

TABLE 1

| Developer (ratio by volume) | $R_f$ value |
|---|---|
| toluene:acetone (7:3) | 0.30 |
| n-hexane:ethyl acetate:acetic acid (50:75:0.5) | 0.32 |

After the development, the spots of DC-89A1 can be detected by bioassay using *Bacillus subtilis*, by color reaction using hot sulfuric acid, iodine or Ehrlich's reagent, or under ultraviolet lamp.

Biological properties of DC-88A and DC-89A1 are shown below.

(A) Minimum inhibitory concentration against various microorganisms (MIC μg/ml)

TABLE 2

| Microorganism | MIC (μg/ml) DC-88A | MIC (μg/ml) DC-89A1 |
|---|---|---|
| *Staphylococcus aureus* ATCC 6538P | 0.05 | >8.4 |
| *Bacillus subtilis* No. 10707 | 0.05 | 0.07 |
| *Klebsiella pneumoniae* ATCC 10031 | 0.5 | 4.2 |
| *Escherichia coli* ATCC 26 | 20.0 | >100 |
| *Shigella sonnei* ATCC 9290 | 40.0 | — |
| *Salmonella typhi* ATCC 9992 | 10.0 | >100 |

The antibacterial activity was measured by the agar dilution method, using a medium (pH 7) prepared by dissolving 3 g of Bacto-Tryptone (Manufactured by Difco Co., Ltd.), 3 g of meat extract, 1 g of yeast extract, 1 g of glucose and 16 g of agar in 1 l of water.

(B) Acute toxicity

The acute toxicity values ($LD_{50}$) of DC-88A and DC-89A1 were about 0.94 mg/kg and about 1.17 mg/kg, respectively, by intraperitoneal administration to mice.

(C) Anti-tumor activity (1) Therapeutic effect against Sarcoma 180 solid tumor

Six male ddY-strain mice each having a weight of about 20 g were used for each group as test animals, and $5 \times 10^6$ cells of Sarcoma 180 ascites tumor were implanted subcutaneously into the animals at the axilla. 0.2 ml of phosphate buffered saline (hereinafter referred to as PBS) containing DC-88A or DC-89A1 at the concentrations shown in Tables 3 and 4 was administered once intraperitoneally 24 hours after implantation.

The composition of PBS was 0.8 g/dl NaCl, 0.02 g/dl KCl, 1.15 g/dl $Na_2HPO_4$ and 0.02 g/dl $KH_2PO_4$ (pH 7.2).

The average tumor volume ($mm^3$) and T/C [T: average tumor volume of the groups treated with the test compound ($mm^3$), C: that of control group which received an intraperitoneal administration of 0.2 ml of PBS solution ($mm^3$)] were determined ten days after implantation. The results are shown in the following Tables 3 and 4.

TABLE 3

| Test Compound | Dosage (mg/kg) | Average Tumor Volume ($mm^3$) | T/C |
|---|---|---|---|
| DC-88A | 0.78 | 467.4 | 0.22 (3/6) |
|  | 0.39 | 849.9 | 0.40 |
|  | 0.195 | 1104.8 | 0.52 |

TABLE 3-continued

| Test Compound | Dosage (mg/kg) | Average Tumor Volume ($mm^3$) | T/C |
|---|---|---|---|
| Control | — | 2124.7 | — |

TABLE 4

| Test Compound | Dosage (mg/kg) | Average Tumor Volume ($mm^3$) | T/C |
|---|---|---|---|
| DC-89A1 | 1.5625 | Toxic | |
|  | 0.78125 | 1409.5 | 0.77 |
| Control | 0 | 1828.0 | — |
| Mitomycin C | 6 | 499.6 | 0.27 |

For comparison, 0.2 ml of PBS containing mitomycin C was intraperitoneally administered to a group of animals 24 hours after tumor implantation.

(2) Therapeutic effect on lymphocytic leukemia P388 tumor

Five male $CDF_1$ mice each having a weight of about 22 g were used for each group as test animals, and $1 \times 10^6$ cells of lymphocytic leukemia P388 tumor were implanted intraperitoneally into the test animals. 0.2 ml of PBS containing DC-88A or DC-89A1 was administered once intraperitoneally 24 hours after implantation. The mean survival days after implantation and increased life span (T/C) (T: mean survival days for the treated groups, C: mean survival days for the control group) were calculated. The results are shown in Tables 5 and 6.

TABLE 5

| Test Compound | Dosage (mg/kg) | Mean Survival Days | Increased Life Span (T/C) |
|---|---|---|---|
| Control | 0 | 11.0 | — |
| DC-88A | 0.78 | 12.3 | 1.12 |
|  | 0.39 | 12.5 | 1.14 |
|  | 0.195 | 12.7 | 1.15 |
|  | 0.098 | 11.9 | 1.08 |
|  | 0.024* | 15.7 | 1.43 |

*Continuous administration for five days

TABLE 6

| Test Compound | Dosage (mg/kg) | Mean Survival Days | Increased Life Span (T/C) |
|---|---|---|---|
| DC-89A1 | 1 | 13.2 | 1.23 |
|  | 0.5 | 15.0 | 1.40 |
|  | 0.25 | 14.8 | 1.38 |
|  | 0.125 | 13.8 | 1.28 |
|  | 0 | 10.7 | — |
| Mitomycin C | 6.0 | 17.2 | 1.60 |

For comparison, 0.2 ml of PBS solution containing mitomycin C was intraperitoneally administered to a group of animals 24 hours after tumor implantation.

The process for producing DC-88A and DC-89A1 is described below.

DC-88A and/or DC-89A1 can be obtained by culturing DC-88A- and/or DC-89A1-producing strains belonging to the genus Streptomyces in a nutrient medium, and recovering DC-88A and/or DC-89A1 from the culture broth. As the DC-88A- and/or DC-89A1-producing strains, any microorganisms can be used so long as they belong to the genus Streptomyces and have an ability to produce DC-88A and/or DC-89A1.

As the typical strains to be used, DO-88 strain and DO-89 strain described above are mentioned.

Microbiological properties of DO-88 strain are as follows.

(1) Morphology

| | |
|---|---|
| Aerial mycelium | It is branched but not fragmented. |
| Substrate mycelium: | It is not fragmented. |
| Spore | Long spiral chains of spores are formed at the end of simply branched aerial mycelium. |
| Surface of spore | Smooth |
| Shape and size of spore | Oval, about 0.7 × 0.9 μm |
| Motility of spore | Negative |

No formation of sclerotium and sporangium is observed.

(2) Color

| | |
|---|---|
| Aerial mycelium | Gray |
| Substrate mycelium | Beige to brown |
| Soluble pigment | None |
| Melanoid-like pigment | None |

(3) Chemical composition of cell wall
Steric configuration of diaminopimelic acid: LL type (4) Cultural characteristics on various medium
Cultural characteristics of DO-88 strain on various agar media observed after culturing at 28° C. for 3 weeks are shown in Table 7.

TABLE 7

| Medium | Cultural Characteristics |
|---|---|
| Sucrose-nitrate agar medium | G: poor<br>AM: fair, light mustard tan (2ie)<br>SM: light mustard tan (2ie) to beige (3ge) |
| Glucose-asparagine agar medium | G: good, raised<br>AM: abundant, natural (2dc) to covert tan (2ge)<br>SM: covert tan (2ge) to natural (2dc) |
| Glycerine-asparagine agar medium | G: good, raised<br>AM: abundant, covert gray (2fe) to pearl (3ba)<br>SM: covert tan (2ge) |
| Starch agar medium | G: good, raised<br>AM: abundant, natural (2dc) to covert gray (2fe)<br>SM: mustard tan (21g) |
| Tyrosine agar medium | G: moderate<br>AM: fair, covert tan (2ge)<br>SM: biscuit (2ec) |
| Nutrient agar medium | G: moderate<br>AM: fair, silver gray (3fe) to pearl (3ba)<br>SM: natural (2dc) |
| Yeast extract - malt extract agar medium | G: good, raised<br>AM: abundant, pearl (3ba) to dark brown (2pn)<br>SM: mustard brown (2pl) |
| Oatmeal agar medium | G: good, raised<br>AM: abundant, pearl (3ba) to covert gray (2fe)<br>SM: covert brown (2li) |
| Peptone-yeast extract-iron agar medium | G: good, granular<br>AM: none<br>SM: honey gold (2ic) |

Note (1) Color indication: Color Harmony Manual, Container Corporation of America
Note (2) G: growth
AM: formation of aerial mycelium and its color
SM: color of substrate mycelium
Note (3) No formation of soluble pigments and melanoid-like pigments was observed on any of the culturing media.

(5) Physiological properties
Growth temperature range was determined after 2 days of culturing. The action on defatted milk and cellulose was observed after 1 month of culturing at 28° C. The other observations were made after 2 weeks of culturing at 28° C.

| | |
|---|---|
| Growth temperature range | 20–34° C. |
| Optimum growth temperature range | 26–30° C. |
| Liquefaction of gelatin | Negative |
| Decomposition of cellulose | Slightly positive |
| Coagulation and peptonization of defatted milk | Both positive |
| Hydrolysis of starch | Positive |
| Formation of melanin-like pigment | Negative |
| Assimilation of carbon sources | |
| D-Glucose | + |
| L-Arabinose | + |
| D-Xylose | + |
| Inositol | + |
| D-Mannitol | + |
| D-Fructose | + |
| L-Rhamnose | + |
| Sucrose | + |
| Raffinose | + |

(+: assimilated as a single carbon source)

(6) Identification of DO-88 strain
The cell wall of DO-88 strain contains LL-diaminopimelic acid. Therefore, this strain belongs to the Type I cell wall group according to the classification by Lechevalier, et al. [International Journal of Systematic Bacteriology, 20, 435–443 (1970)]. Morphological characteristics such as formation of aerial mycelia simply branched and formation of long spore chains at the end thereof indicate that this strain belongs to the genus Streptomyces in Actinomycetales.

A search was made through the Approved Lists of Bacterial Names of International Code of Nomenclature of Bacteria [International Journal of Systematic Bacteriology, 30, 225–420 (1980); ibid., 35, 382–407 (1985)] for a strain having microbiological properties akin to those of DO-88 strain according to the searching method of Nonomura [Journal of Fermentation Technology, 52, 79–92 (1974)] and the description of the International Streptomyces Project [International Journal of Systematic Bacteriology, 18, 69–189 (1968); ibid., 18, 279–392 (1968); ibid., 19, 391–512 (1962); ibid., 22, 265–394 (1972)].

Keys for the search are as follows:

| | |
|---|---|
| Color of aerial mycelium | Gray |
| Sporophore | Spiral |
| Surface of spore | Smooth |
| Formation of melanin-like pigment and soluble pigment | None |
| Pattern of utilization of carbon sources | |

As a result of the search, *Streptomyces parvullus, Streptomyces lydicus, Streptomyces thermovulgaris, Streptomyces misionensis, Streptomyces libani*, etc. were selected.

Comparison in more detail revealed that *Streptomyces lydicus* and *Streptomyces libani* are different from DO-88 strain in that the colors of back sides of colonies contain orange and yellow, and further *Streptomyces libani* forms a slight amount of yellowish soluble pigments. Furthermore, unlike DO-88 strain, *Streptomyces misionensis* has aerial mycelia of a reddish color and *Streptomyces thermovulgaris* grows in the temperature range of 40°–50° C. On the other hand, the microbiological characteristics of *Streptomyces parvullus* show comparative resemblance to those of DO-88 strain.

Therefore, DO-88 strain was identified as *Streptomyces parvullus*, named *Streptomyces parvullus* DO-88, and deposited with the Fermentation Research Institute, Agency of Industrial Science and Technology under FERM BP-1002 on Mar. 24, 1986.

Microbiological properties of DO-89 strain are as follows.

Morphology

| Aerial mycelium | It is branched but not fragmented. |
| --- | --- |
| Substrate mycelium | It is not fragmented. |
| Spore | Spiral chains of spores are formed at the end of simply branched aerial myselium. |
| Surface of spore | Smooth |
| Shape and size of spore | Oval, 0.5–0.7 μm × 0.8–1.2 μm |
| Motility of spore | Negative |

Color

| Aerial mycelium | Gray |
| --- | --- |
| Substrate mycelium | Gray, beige or brown |
| Soluble pigment | None |

Chemical composition of cell wall
Steric configuration of diaminopimelic acid: LL type
Assimilation of carbon sources

| Carbon Source | Growth |
| --- | --- |
| D-Glucose | ++ |
| L-Arabinose | ++ |
| D-Xylose | ++ |
| Inositol | ++ |
| D-Mannitol | ++ |
| D-Fructose | + |
| L-Rhammose | ++ |
| Sucrose | + |
| Raffinose | + |

+: moderate growth
++: good growth

| Liquefaction of gelatin | Negative |
| --- | --- |
| Hydrolysis of starch | Positive |
| Coagulation and peptonization of defatted milk: | Both positive |
| Formation of melanin-like pigment | None |
| Decomposition of cellulose | Negative |
| Growth temperature range (optimum) | 21–37° C. (30–32° C.) |

Growth temperature range was determined after 2 days of culturing. The action on defatted milk and cellulose was observed after 1 month of culturing at 28° C. The other observations were made after 2 weeks of culturing at 28° C.

Cultural Characteristics on Various Agar Media

| Culturing: | 28° C., 21 days |
| --- | --- |
| Color indication: | Color Harmony Manual, Container Corporation of America |
| Medium | Cultural Characteristics |
| Sucrose-nitrate agar medium | G: good, smooth AM: abundant, beige brown (3ig) SM: dark covert gray (2ih) |
| Glucose-asparagine agar medium | G: poor, smooth AM: poor, natural (3dc) SM: silver gray (3fe) |
| Glycerine-asparagine | G: good, granular |

| -continued | |
| --- | --- |
| Culturing: | 28° C., 21 days |
| Color indication: | Color Harmony Manual, Container Corporation of America |
| Medium | Cultural Characteristics |
| agar medium | AM: abundant, white (a) to covert gray (2fe) SM: olive gray (2ml) |
| Starch agar medium | G: moderate, smooth AM: poor, white (a) to covert gray (2fe) SM: olive gray (2ml) |
| Tyrosine agar medium | G: moderate, granular AM: fair, dark covert gray (2ih) SM: beige brown (3ig) |
| Nutrient agar medium | G: moderate, granular AM: fair, covert gray (2fe) SM: citron gray (1fe) |
| Yeast extract - malt extract agar medium | G: moderate, granular AM: abundant, covert gray (2fe) SM: golden brown (3pi) |
| Oatmeal agar medium | G: good, raised AM: abundant, silver gray (3fe) SM: ebony (1po) |
| Peptone-yeast extract-iron agar medium | G: moderate, smooth AM: none SM: light wheat (2ea) |

G: growth
AM: formation of aerial mycelium and its color
SM: color of substrate mycelium No formation of soluble pigments was observed on any of the culturing media.

Cell wall composition

As a result of the analysis of diaminopimelic acid which is one of the cell wall amino acids, LL-2,6-diaminopimelic acid was detected but meso-diaminopimelic acid was not detected.

The strain forms aerial mycelia which are simply branched, and long chains of spores are formed at the end of the mycelia. Further, the cell wall contains LL-diaminopimelic acid. Therefore, this strain is classified as a strain of the genus Streptomyces in Actinomycetales.

A search was made for a strain having microbiological properties akin to those of DO-89 strain among the approved microbiological species.

Keys for the search are as follows.

| Sporophore | Spiral |
| --- | --- |
| Surface of spore | Smooth |
| Formation of melanin-like pigment | None |
| Pattern of utilization of carbon sources | |
| Colors on the culturing media | |

As a result of the search, *S. parvullus, S. lydicus, S. thermovulgaris, S. misionensis, S. libani*, etc. were selected.

Comparison in more detail revealed the differences between most of them and DO-89 strain. That is, *S. parvullus* has greenish substrate mycelia and the optimum growth temperature range of *S. thermovulgaris* is 40°–50° C. *S. misionensis* has reddish aerial mycelia and *S. libani* forms a slight amount of soluble pigments.

On the other hand, *Streptomyces lydicus* shows the most close resemblance to DO-89 strain. Therefore, DO-89 strain was identified as *Streptomyces lydicus*, named *S. lydicus* DO-89 and deposited with the Fermentation Research Institute, Agency of Industrial Science and Technology under FERM BP-988 on Feb. 13, 1986.

As is the case with known strains of the genus Streptomyces, the above-mentioned microorganisms can be mutated by artificial means such as ultraviolet irradiation, X-ray irradiation and the treatment with various mutagens. Even mutants thus prepared can be used in the present invention insofar as they have the ability to produce DC-88A and/or DC-89A1.

As the medium for culturing in the present invention, either a natural medium or a synthetic medium may be used so long as it appropriately contains carbon sources, nitrogen sources and inorganic materials.

As the carbon source, glucose, starch, dextrin, glycerol, mannose, fructose, sucrose, molasses, alcohols such as methanol and ethanol, organic acids such as acetic acid, formic acid, citric acid and malic acid, etc. are used.

As the nitrogen source, ammonium chloride, ammonium sulfate, ammonium nitrate, sodium nitrate, urea, peptone, meat extract, yeast extract, dry yeast, corn steep liquor, soybean powder, Casamino acid, etc. are used.

As the inorganic materials, sodium chloride, potassium chloride, ferrous sulfate, zinc sulfate, manganese sulfate, copper sulfate, nickel sulfate, potassium dihydrogen phosphate, dipotassium hydrogen phosphate, magnesium phosphate, magnesium sulfate, calcium carbonate, etc. are used.

In addition, substances for acclerating production of DC-88A or DC-89A1, for example, biotin, vitamins, etc. may also be supplemented to the medium.

Culturing is usually carried out by liquid culture, and most preferably by submerged stirring culture. Culturing temperature is 25° to 33° C., preferably 28° to 30° C. It is desirable to maintain the pH of the medium at 4 to 10, preferably 6 to 8 by adding aqueous ammonia or aqueous ammonium carbonate during the culturing.

Usually, by liquid culture for 1 to 7 days, DC-88A and/or DC-89A1 are produced and accumulated in the culture broth. Preferably, when the amount of the products in the culture broth reaches the maximum, culturing is discontinued.

DC-88A and/or DC-89A1 are isolated and purified from the culture filtrate after the microbial cells have been removed by filtration. If necessary, the microbial cells are extracted with a solvent such as chloroform, acetone, etc., and the extract can also be used.

For the isolation and purification of DC-88A and/or DC-89A1 from the culture filtrate, an ordinary method for isolating a microbial metabolite from the culture broth can be utilized.

For example, the culture filtrate is passed through a column packed with a non-ionic porous resin such as HP-20 (manufactured by Mitsubishi Chemical Industries Ltd.) to adsorb the active component. Then, the adsorbed active component is eluted with methanol, ethyl acetate or acetone.

The eluate is concentrated and purified using silica gel (Wakogel C-200, Wako Pure Chemical Industries, Ltd.), etc. The product is further purified using silica gel (LiChroprep Si60, Merck), etc. and then using reverse phase silica gel (Wakogel L.C-ODS, Wako Pure Chemical Industries, Ltd.), etc. to obtain DC-88A and/or DC-89A1. The thus obtained DC-88A can be further purified to elevate the purity by procedures such as recrystallization, high performance liquid chromatography, etc.

Prior to the silica gel column chromatography, water of pH 5-6 and ethyl acetate may be added to the concentrate, followed by shaking, whereby the active component is shifted to the ethyl acetate layer.

The ethyl acetate layer is concentrated to dryness to give crude DC-88A and/or DC-89A1 as a powder.

DC-88A and/or DC-89A1 themselves and compositions comprising effective amounts of them and vehicles can be used as antibiotics and anti-tumor agents. The vehicle contains diluents, excipients, disintegrators, binders, lubricants, bases, etc. which are commonly used.

When the compound is administered in the form of injection, for example, the compound is dissolved in diluents which are commonly used in the field of pharmaceutics such as ethanol, optionally with a surfactant and a solubilizing agent, and after ethanol is sucked off if necessary, the solution is mixed with distilled water for injection, physiological saline solution, or a distilled water for injection containing glucose, fructose, mannitol, etc.

Alternatively, the ethanol solution may be freeze-dried or the compound may be mixed with sodium chloride to prepare a powder preparation for injection, which is dissolved before each application. These injections are administered, for example, intravenously. Intramuscular administration, intraarterial administration, intraperitoneal administration, intrathoracic administration, etc. are also possible. Preparations for oral administration are prepared by mixing DC-88A and/or DC-89A1 with a suitable excipient, disintegrator, binder, lubricant, etc. and forming the mixture into tablets, granules or powders in a conventional manner.

Although the amount of the compound for dosage varies in accordance with the method of administration, the age and condition of patients, etc., it is suitable to administer the compound in an amount of 0.5 to 75 mg/60 kg per day to mammals including human beings.

EXAMPLE

Figure 1:
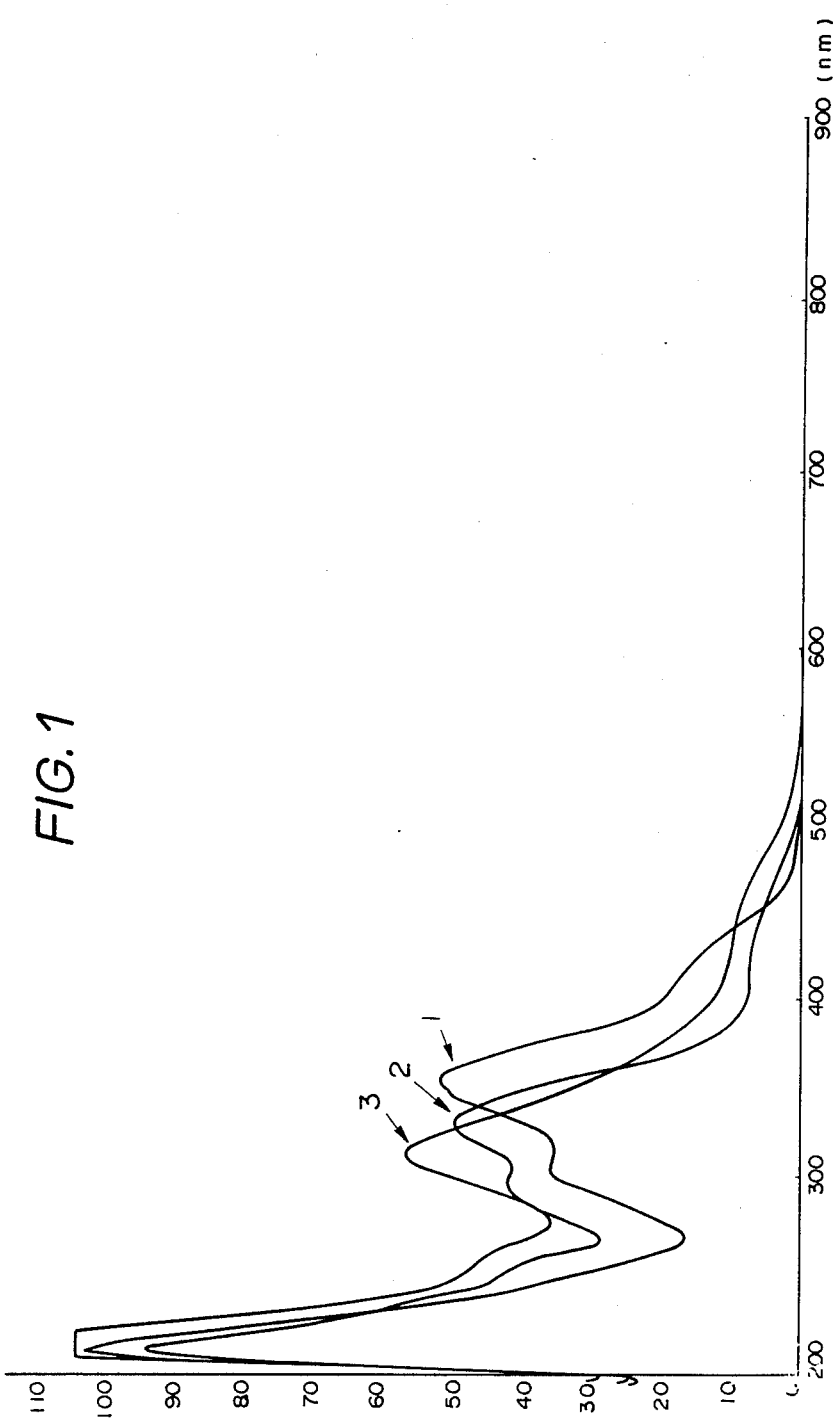
FIG. 1 and FIG. 3 show the ultraviolet absorption spectra (in $CH_3OH$ solution) of DC-88A and DC-89A1, respectively, in which 1 or the solid line represents the data under neutral conditions, 2 or the broken line the data under acidic conditions (0.01N HCl), and 3 or the dot and dash line the data under alkaline conditions (0.01N NaOH).
Figure 2:
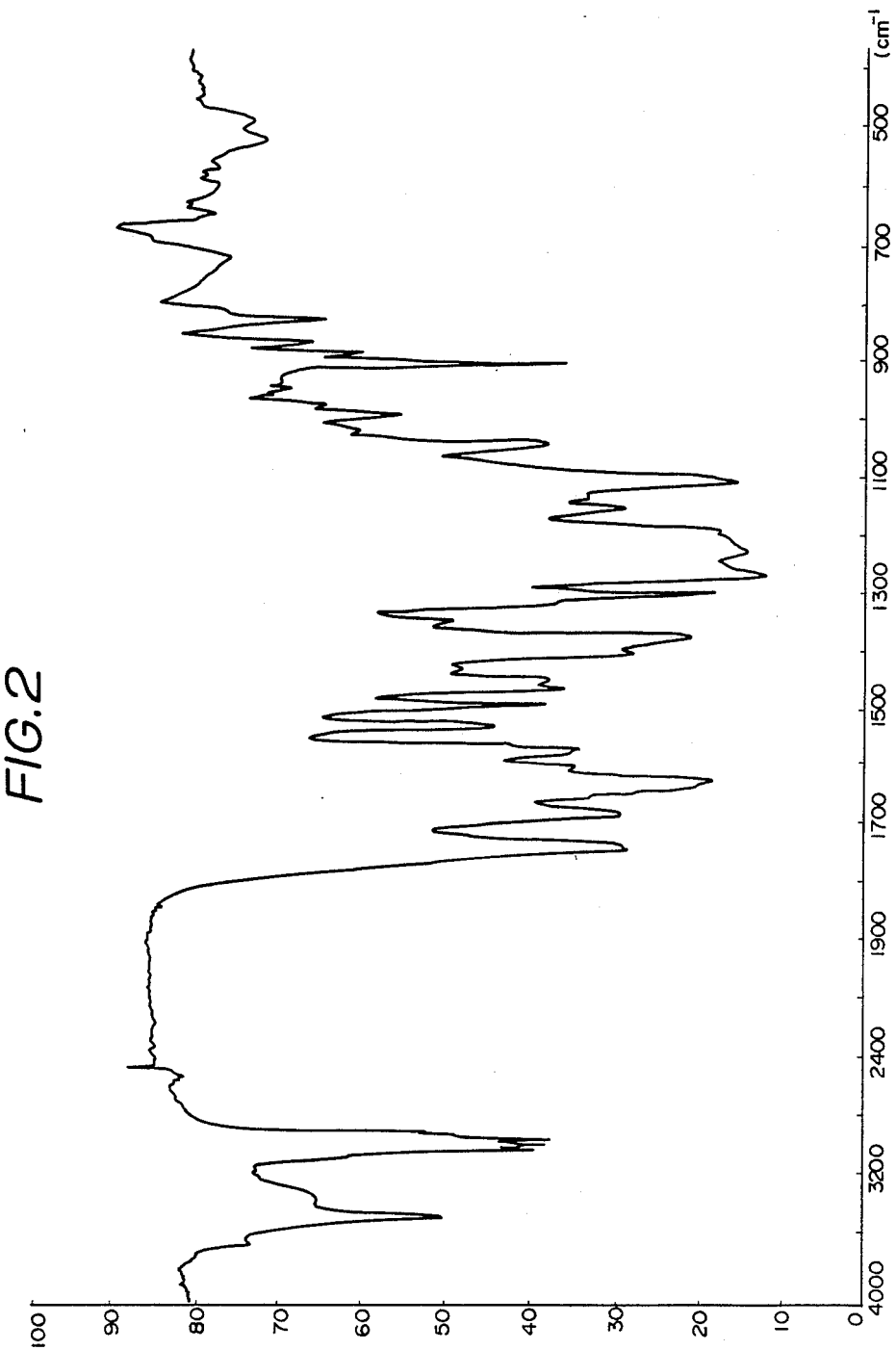
FIG. 2 and FIG. 4 show the infrared absorption spectra (in $CHCl_3$ solution) of DC-88A and DC-89A1, respectively.
Figure 3:
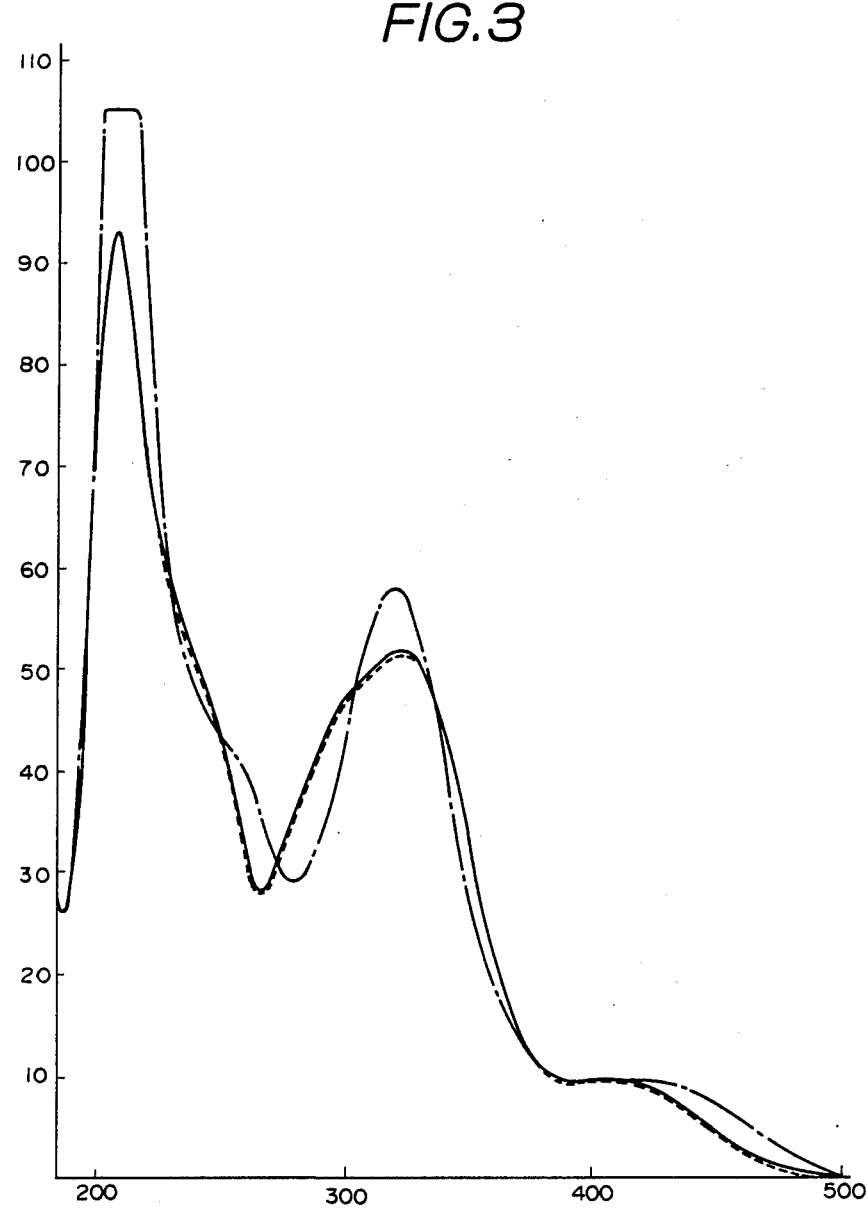
Figure 4:
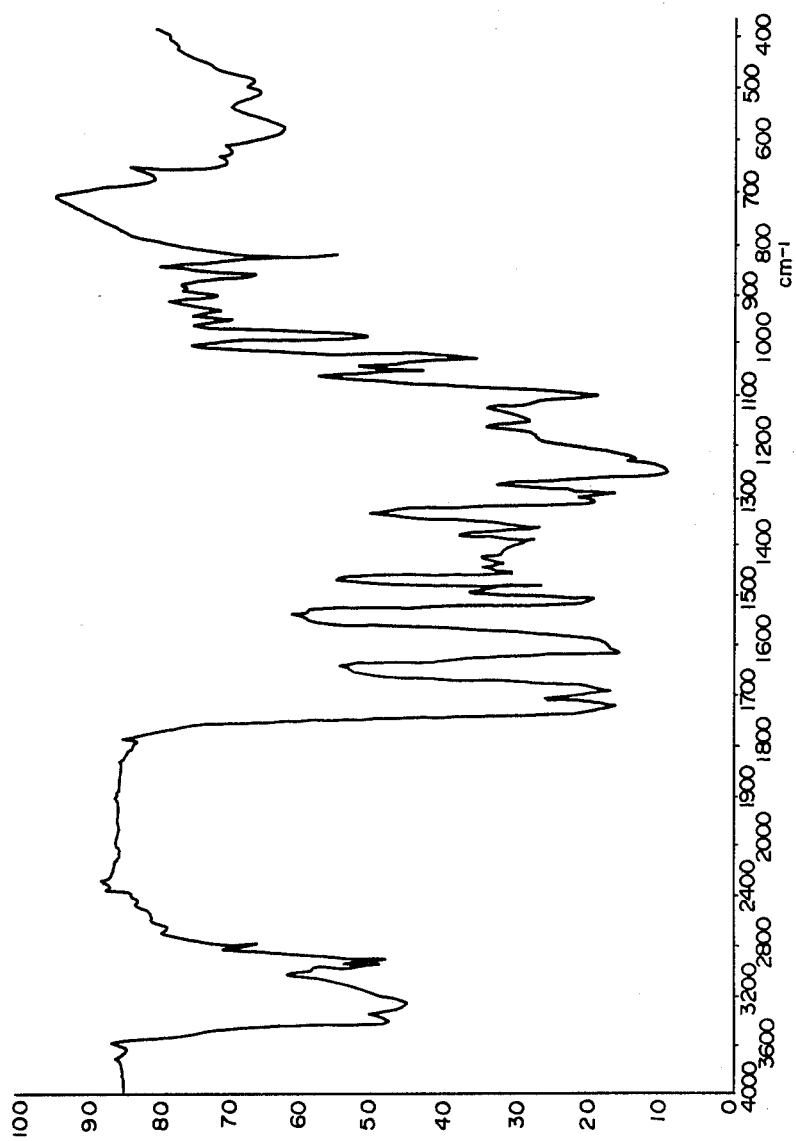

Examples of the present invention are shown below. In the examples, DC-88A and DC-89A1 were traced by bioassay using *Bacillus subtilis* No. 10707, or by detection under ultraviolet lamp after thin layer chromatography.

EXAMPLE 1

*Streptomyces parvullus* FERM BP-1002 was used as a seed strain. The strain was inoculated in 300 ml of a seed medium (pH 7.2, prior to sterilization) containing 20 g/l dextrin, 10 g/l peptone, 1 g/l yeast extract, 5 g/l corn steep liquor, 10 g/l glucose and 5 g/l calcium carbonate in a 2 l-Erlenmeyer flask and subjected to shaking culture (200 rpm) at 30° C. for 48 hours. The resulting seed culture was inoculated in 15 l of a fermentation medium having the following composition in a 30 l-jar fermentor, and cultured at 30° C. with aeration and stirring (rotation: 250 rpm, aeration: 15 l/min).

Composition of the fermentation medium: 20 g/l soluble starch, 5 g/l dry yeast, 0.5 g/l $KH_2PO_4$, 0.5 g/l $MgSO_4.7H_2O$, 5 g/l calcium carbonate (pH 7.0, adjusted with NaOH prior to sterilization)

Culturing was carried out for 72 hours, during which the pH of the medium was adjusted to 6.5–7.5 with aqueous ammonia.

The microbial cells were separated from the culture broth by filtration to give 13 l of a filtrate. Then, 13 l of the filtrate was passed through a column filled with 2 l of nonionic porous resin HP-20 (trademark, manufactured by Mitsubishi Chemical Industries Ltd.) to adsorb the active component. After being washed with water, the column was further washed with 50% methanol to remove impurities. Then, after being washed with water again, the column was eluted with ethyl acetate. The eluted fractions were concentrated and developed with toluene-acetone using silica gel (Wakogel C-200, Wako Pure Chemical Industries, Ltd.) to obtain an active component. The active component was then developed with toluene-acetone using silica gel (LiChroprep Si60, Merck) to obtain crude DC-88A. The crude product was subjected to density gradient elution using high performance liquid chromatography (Wakogel-L.C-ODS 30 k, Wako Pure Chemical Industries, Ltd.) with 50% to 100% methanol to obtain 3 mg of DC-88A. The thus obtained DC-88A showed the physicochemical properties and biological properties described hereinbefore.

EXAMPLE 2

The same procedures as described in Example 1 were repeated except that *Streptomyces lydicus* FERM BP-988 was used as a seed strain, whereby 1.8 mg of DC-88A was obtained.

EXAMPLE 3

*Streptomyces lydicus* FERM BP-988 was used as a seed strain. The strain was inoculated in 300 ml of a seed medium (pH 7.2, prior to sterilization) containing 5 g/l Bacto-Tryptone (manufactured by Difco Co., Ltd.), 5 g/l yeast extract, 3 g/l meat extract, 10 g/l soluble starch, 10 g/l glucose and 5 g/l calcium carbonate in a 2 l-Erlenmeyer flask and subjected to shaking culture (200 rpm) at 30° C. for 48 hours. The resulting seed culture was transferred in an amount of 5% by volume into 15 l of a medium having the same composition as mentioned above in a 30 l-jar fermentor, and cultured at 28° C. for 24 hours with stirring (rotation: 200 rpm, aeration: 15 l/min).

The resulting culture was then transferred in an amount of 10% by volume into 150 l of a fermentation medium having the following composition in a 200 l-tank fermentor, and cultured at 28° C. with aeration and stirring (rotation: 200 rpm, aeration: 15 l/min).

Composition of the fermentation medium: 50 g/l dextrin, 10 g/l dry yeast, 10 g/l $NaNH_4HPO_4.4H_2O$, 0.5 g/l $KH_2PO_4$, 0.5 g/l $MgSO_4.7H_2O$, 10 g/l potassium chloride, 5 g/l calcium carbonate (pH 7.2, adjusted with NaOH prior to sterilization)

Culturing was carried out for 70 hours without controlling the pH of the medium. The microbial cells and other precipitates formed were separated from the culture broth by filtration to give 100 l of a filtrate.

30 l of acetone was added to the microbial cells and other precipitates, and the suspension was allowed to stand overnight. Then, the acetone extract was filtrated and the filtrate (25 l) was diluted with 75 l of water. The diluted filtrate and the culture filtrate were combined (total volume: 200 l), adjusted to pH 5.0 with hydrochloric acid, and then passed through a column filled with 10 l of Diaion HP-20 to adsorb the active component. After the column was washed with water and then with 40% methanol solution, elution was carried out with methanol. The eluted fractions were concentrated and adjusted to pH 6.0, followed by extraction with ethyl acetate.

The extract was concentrated and the residue was mixed with silica gel (Wakogel C-200, Wako Pure Chemical Industries, Ltd.) to obtain a powder. The powdery sample was applied to a column filled with 1000 ml of silica gel (Wakogel C-200, Wako Pure Chemical Industries, Ltd.) previously suspended in n-hexane. Then, a mixed solvent of n-hexane, ethyl acetate and acetic acid (600:300:4 V/V/V) was passed through the column to remove impurities. Elution was carried out with the above solvent system in which the rate of ethyl acetate was increased stepwise. Finally, a mixed solvent of n-hexane, ethyl acetate and acetic acid (225:675:4 V/V/V) was passed through the column to obtain active fractions. The fractions were concentrated and mixed with silica gel (LiChroprep Si60, Merck) to obtain a powder. The powdery sample was applied to a column filled with 50 ml of silica gel (LiChroprep Si60, Merck) previously suspended in n-hexane, and a mixed solvent of n-hexane, ethyl acetate and acetic acid (400:100:2.5 V/V/V) was passed through the column under a pressure of 5 kg/cm$^2$ to remove impurities.

Then, elution was carried out under a pressure of 5 kg/cm$^2$ with the above solvent system in which the rate of ethyl acetate was increased stepwise. Finally, a mixed solvent of n-hexane, ethyl acetate and acetic acid (250:250:2.5 V/V/V) was passed through the column under a pressure of 5 kg/cm$^2$ to elute active fractions. The active fractions were concentrated to dryness and the residue was dissolved in a small amount of acetonitrile. The solution was applied to a column filled with chemically modified silica gel (Wakogel LC $NH_2$-10H, Wako Pure Chemical Industries, Ltd.) previously suspended in acetonitrile. Then, density gradient elution was carried out with 100% acetonitrile to 90% aqueous acetonitrile solution. The active fractions were combined and concentrated to obtain 10 mg of pure DC-89A1. The thus obtained DC-89A1 showed the physicochemical properties, antibacterial activity and antitumor activity described hereinbefore.

EXAMPLE 4

The same fermentation procedures as described in Example 1 were repeated except that *Streptomyces parvullus* FERM BP-1002 was used and 5 g/l $NH_4Cl$ was added to the fermentation medium. Thin layer chromatography showed that DC-89A1 was mainly produced in the culture broth, while DC-88A was accumulated in a trace amount.

Purification and isolation of DC-89A1 from the culture broth were carried out in the same manner as described in Example 1 to obtain 8 mg of DC-89A1.

EXAMPLE 5

Injection 10 mg of DC-89A1 obtained in Example 3 was dissolved in 50 ml of ethanol. The solution was stirred and ethanol was sucked off. The residue was dissolved in about 10 ml of sterilized physiological saline solution to give a solution for injection.
We claim:
1. DC-88A, a compound of the formula
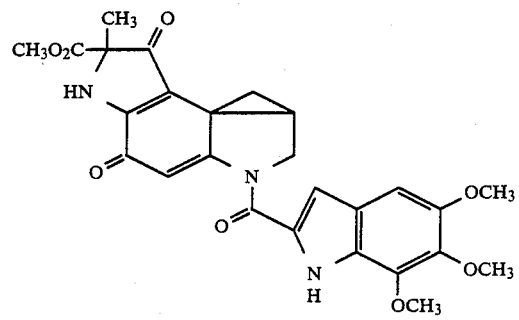
2. DC-89A1, a compound of the formula
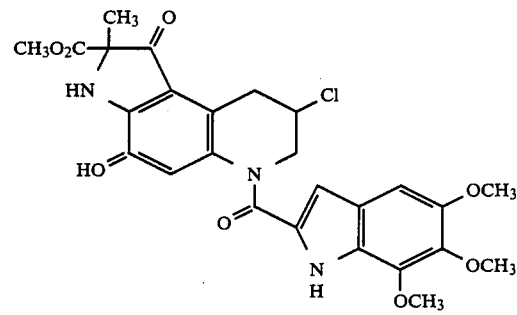
* * * * *

UNITED STATES PATENT AND TRADEMARK OFFICE
CERTIFICATE OF CORRECTION

PATENT NO. : 4,923,990

DATED : May 8, 1990

INVENTOR(S) : Nakano et al

It is certified that error appears in the above-identified patent and that said Letters Patent is hereby corrected as shown below:

On the title page item [54] and in column 1, lines 1-3 "PYRINDAMYCINS A AND B AND DUOCARMYCIN A ANTIBIOTICS DERIVED FROM CERTAIN STREPTOMYCES CULTURE" should read --PYRINDAMYCINS A AND B AND DUOCARMYCIN A AND C1 ANTIBIOTICS DERIVED FROM CERTAIN STREPTOMYCES CULTURE--.

Column 9, line 28 "acclerating" should read --accelerating--.

Column 14, lines 17-28, the formula should read

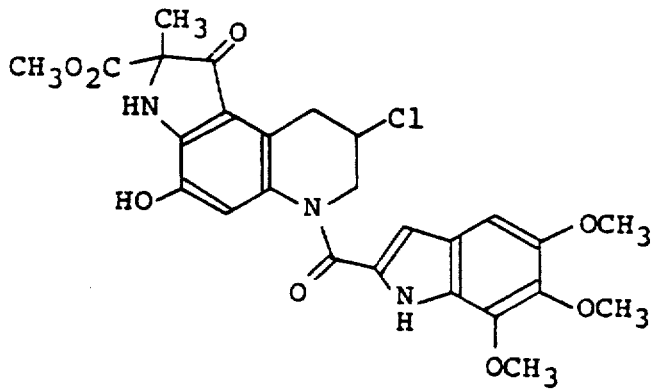

Signed and Sealed this

Eighteenth Day of February, 1992

Attest:

HARRY F. MANBECK, JR.

*Attesting Officer*   *Commissioner of Patents and Trademarks*